United States Patent
Baccelli (10) Patent No.: US 6,306,136 B1
(45) Date of Patent: Oct. 23, 2001

(54) IMPLANT, IN PARTICULAR FRONT CERVICAL PLATE

(75) Inventor: Christian Baccelli, St Medard d'Eyrans (FR)

(73) Assignee: DIMSO (Distribution Medicales du Sud-Ouest) (FR)

( * ) Notice: Subject to any disclaimer, the term of this patent is extended or adjusted under 35 U.S.C. 154(b) by 0 days.

(21) Appl. No.: 09/463,714
(22) PCT Filed: Jul. 27, 1998
(86) PCT No.: PCT/FR98/01653
 § 371 Date: Mar. 31, 2000
 § 102(e) Date: Mar. 31, 2000
(87) PCT Pub. No.: WO99/04718
 PCT Pub. Date: Feb. 4, 1999

(30) Foreign Application Priority Data

Jul. 28, 1997 (FR) .................................................. 97 09579

(51) Int. Cl.[7] .................................................. A61B 17/70
(52) U.S. Cl. .................................................. 606/61; 606/71
(58) Field of Search .................................. 606/61, 69, 70, 606/71

(56) References Cited

U.S. PATENT DOCUMENTS

| | | |
|---|---|---|
| 2,443,363 | 6/1948 | Townsend et al. . |
| 3,900,025 | * 8/1975 | Barnes, Jr. . |
| 4,289,123 | * 9/1981 | Dunn . |
| 5,607,428 | 3/1997 | Lin .......................................... 606/69 |
| 5,616,142 | 4/1997 | Yuan et al. .............................. 606/61 |
| 5,707,372 | * 1/1998 | Errico et al. ........................... 606/61 |

FOREIGN PATENT DOCUMENTS

| | | |
|---|---|---|
| 41 32 021 A1 | 4/1993 | (DE) . |
| 0 599 766 A1 | 6/1994 | (EP) . |
| 0 705 572 A2 | 4/1996 | (EP) . |
| 2 728 454 | 6/1996 | (FR) . |

* cited by examiner

Primary Examiner—David O. Reip
(74) Attorney, Agent, or Firm—Lerner, David, Littenberg, Krumholz & Mentlik, LLP (57) ABSTRACT

The invention relates to a plate designed to be fixed with bone fixing screw to two vertebrae. The invention is characterized in that the plate comprises two elements each including at least one hole for a bone fixing screw, each of the elements capable of sliding relative to the other in a direction bringing them closer to or spacing them from the vertebrae relative to each other. The elements are provided with a screw and slot for limiting the mutual sliding travel between them to lock the elements in a given mutual position. The invention is in particular applicable to cervical plates to be implanted from the front of the spine.

21 Claims, 7 Drawing Sheets

FIG_1

FIG_2

FIG_3

FIG_4

FIG_5

FIG_6

FIG. 7

FIG_8

IMPLANT, IN PARTICULAR FRONT CERVICAL PLATE

The present invention relates generally to fixation systems for osteosynthesis of the spine, and it concerns in particular a novel plate, called a cervical plate, intended to join at least two cervical vertebrae in a particular way.

The techniques of bone fusion at the cervical level are well known and are at present practised in indications such as degenerative spine, herniated discs or, more generally, various cases of traumatology or tumours.

These techniques are based on the principle of ablation of a disc, either single or multiple, possibly combined with ablation of a vertebral body, also single or multiple.

The spaces left free by such ablations are generally filled with bone grafts which have been cut to the desired dimensions.

In this connection it is known that, in order to obtain bone fusion using a graft, it is necessary for the latter to be subjected to compressive stresses. This compression is generally obtained by a slight overdimensioning of the graft, combined with surgical distraction between the adjacent cervical bone structures.

The document U.S. Pat. No. 5,616,142 already discloses an implant having a solid plate consisting of two sliding parts, each of which has holes for anchoring screws in two adjacent vertebrae.

With this solid plate it is possible to hold in place the materials which have been introduced between the two vertebrae, such as blocks of hydroxyapatite, bone grafts or even bone substitutes.

Moreover, the ability of the two parts to slide relative to one another makes it possible to adapt easily to different spacings between vertebrae.

However, this known plate has the disadvantage that there is a risk of play between the two parts, and this play can encourage accidental loosening of the screws.

In addition, this possibility of sliding renders the implant incapable of maintaining a desired spacing between the two vertebrae in the longitudinal direction of the spine, so that the initial compression of the bone graft can be adversely affected, with, as a consequence, poor quality or speed of fusion, or even completely defective fusion.

The present invention aims to overcome these disadvantages of the prior art and to make available an implant which can be used particularly as an anterior cervical plate, which is substantially simpler to fit and in which it is possible to use a plate made up of two sliding elements in order to establish and maintain a compression of bone grafts which have been introduced between two vertebrae on which the implant is to be anchored.

Thus, the present invention proposes an implant for osteosynthesis of the spine, comprising a plate intended to be fixed to two vertebrae, such as cervical vertebrae, with the aid of bone fixation screws, in particular by an anterior approach, characterized in that the plate comprises two elements, each including at least one hole for a bone fixation screw, each of the elements being able to slide relative to the other in a direction corresponding to a closing together or distancing of the vertebrae relative to one another, and the said elements being provided with means for limiting the course of the mutual sliding between them and for blocking the said elements in a given mutual position.

Preferred, but non-limiting, features of the implant according to the invention are the following:

The two elements are arranged head to foot.
The two elements are identical.

Each element includes a first end part including the hole or holes for bone fixation screws, and a second end part having an oblong opening whose main axis defines the direction of sliding, the said opening being traversed by a projecting element integral with an intermediate part of the other element.

Each projecting element consists of a screw constituting one of the said blocking means.

The said intermediate part of each element is situated in the extension and continuation of the said first end part.

The said second end part of each element is situated offset in height relative to the said first end part and to the said intermediate part in such a way as to cover the intermediate part of the other element.

Each element additionally comprises a narrower joining part between its intermediate part and its second end part.

The said joining parts of the two elements each delimit part of a through-passage of the plate.

The said through-passage is oblong and has at its base a peripheral shoulder.

The said shoulder is bevelled.

The implant additionally comprises at least one auxiliary anchoring screw engaged in the said through-passage.

The joining part of each element defines at least one shoulder able to cooperate with the second end part or with the intermediate part of the other element, in such a way as to define a limit stop for the sliding of the two elements.

Each bone fixation screw includes an intermediate thread intended to cooperate with a corresponding thread provided in the hole for the associated screw.

Each bone fixation screw includes a head of generally frustoconical contour and provided with a plurality of branches which are separated by interstices of generally axial orientation, the conicity of the head being able to block the screw against rotation by means of the friction of the said head in the associated hole.

The said head has a groove able to cooperate with an inwardly projecting part formed in the associated hole for producing axial blocking.

At least some of the holes for bone fixation screws have an axis not perpendicular to a general plane of the plate.

The invention also proposes a set of implants, characterized in that it comprises a plurality of implants, such as have been defined above, with plate elements which have different numbers of holes for bone fixation screws and different orientations of holes for screws, and a plurality of bone fixation screws, and in that the different plate elements are visibly differentiated.

Other features, aims and advantages of the present invention will become more apparent from reading the following detailed description of preferred embodiments of the said invention, given by way of example and with reference to the attached drawings in which:

Figure 1:
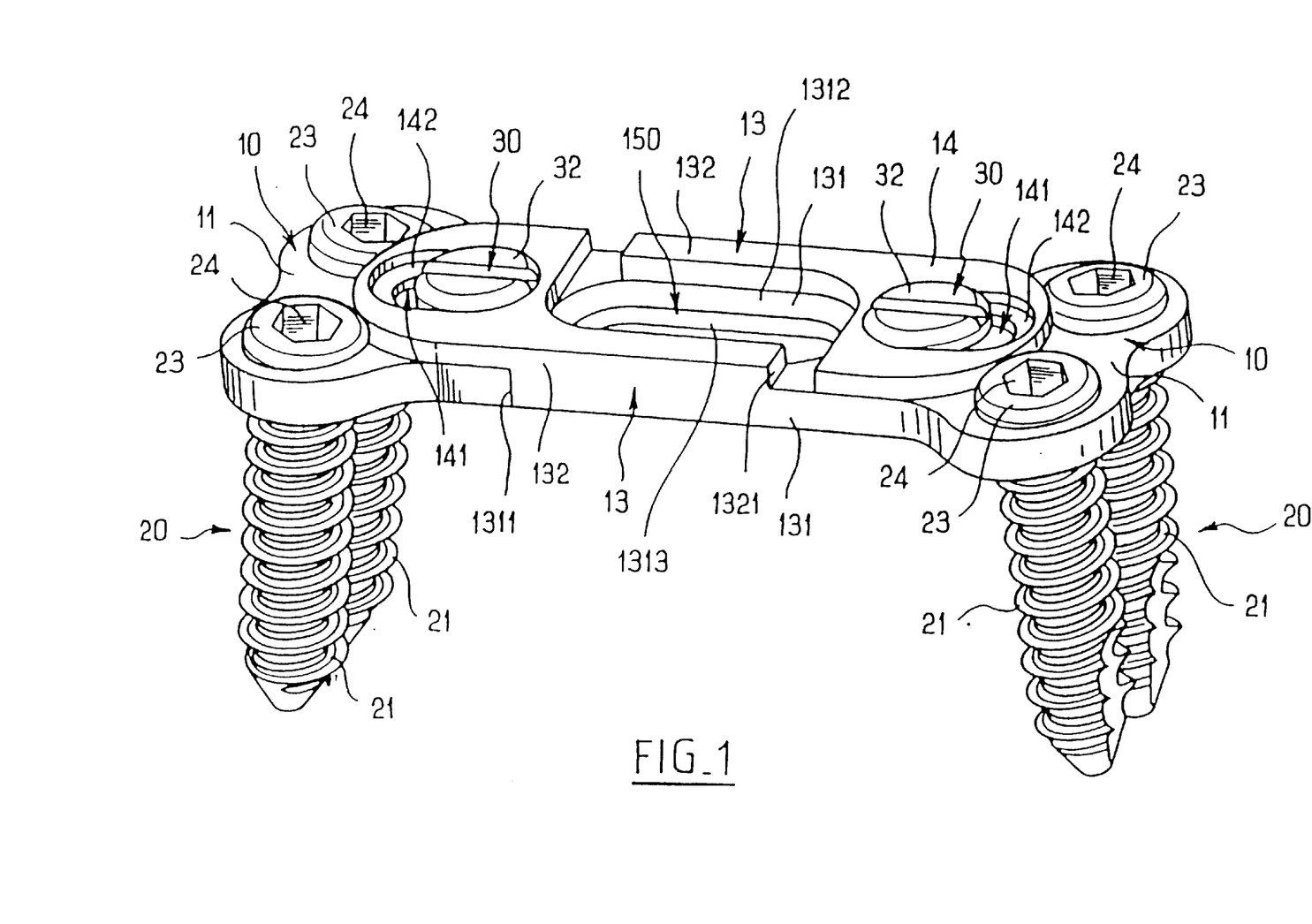
FIG. 1 is a perspective general view of a cervical implant according to the invention.
Figure 2:
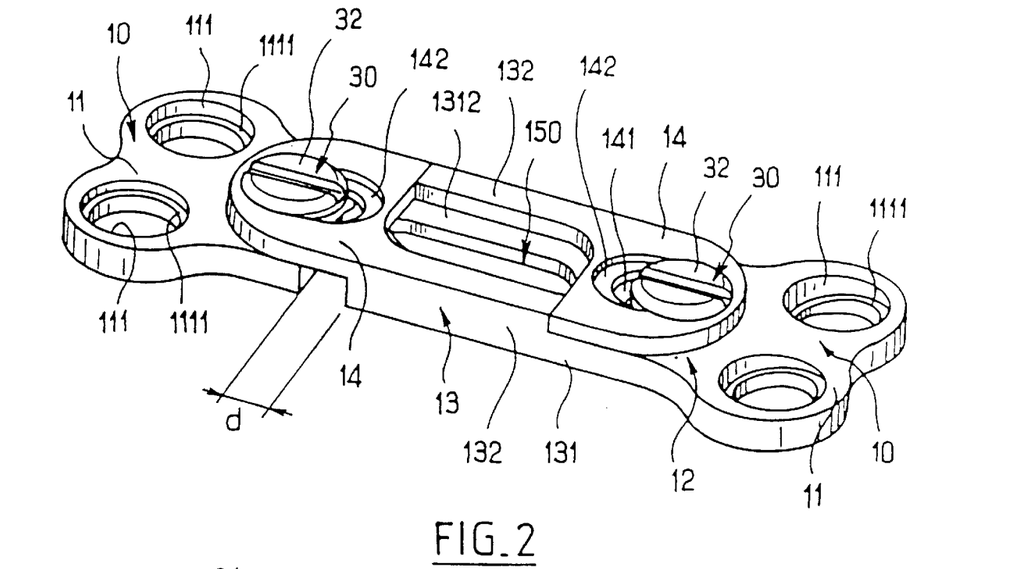
FIG. 2 is a perspective view of the implant in the absence of bone fixation screws.
Figure 3:
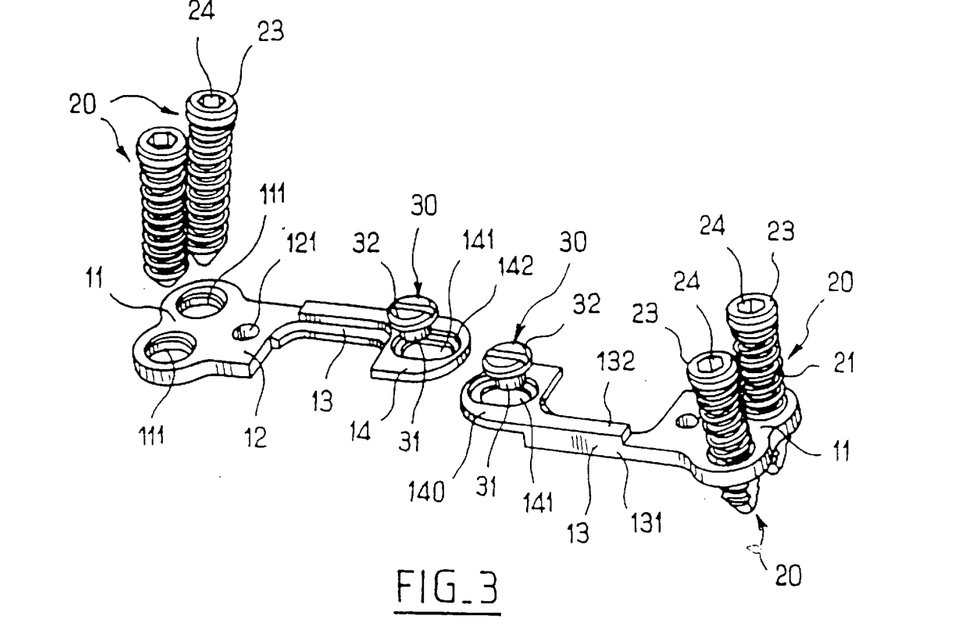
FIG. 3 is an exploded perspective view of the whole implant in FIG. 1.

With reference to the drawing, and firstly to FIGS. 1 to 3, an implant is shown which forms an anterior cervical plate for spinal surgery and which comprises two identical plate elements 10, 10 able to cooperate with bone anchoring screws.

Each plate element comprises an end part 11 for bone anchoring, an intermediate guide part 12, an intermediate joining part 13 and an end guide part 14.

The part 11, in the form of a thin plate with rounded contours, has two generally circular through-openings 111 which are arranged side by side, and inside which a locking thread 1111 is formed, these openings 111 each being intended to receive a bone anchoring screw 20.

The intermediate part 12 extends in the extension of the part 11, over a less extensive width, and has a tapped through-bore 121.

The joining part 13 is generally rectilinear and substantially narrower than the parts 11 and 12, extending in the extension of a side edge of the said part 12. This part 13 has a region 131 situated in the extension of the part 12 in terms of height, and a region 132 which is higher than the region 131. A first transverse cutting 1311 marks the end of the region 131 remote from the part 12, while a second transverse cutting 1321 marks the end of the region 132 towards the part 12.

It will be noted here that the lower region 131 of the joining part 13 has, towards the inside, a greater width than the region 132, being delimited by an internal base face 1313 and by an intermediate bevelled face 1312 joining the face 1313 to the inner face of the region 132. As is shown in particular in FIG. 3, this particular profile adopted by the inside of the region 131 continues along two quarters of a circle, towards the part 12 and towards the part 14.

The part 14 is situated, in terms of height, in the extension of the upper region 132 of the part 13, and it has a width identical to that of the part 12. It ends in an end face of semicircular shape and passing through it there is an oblong opening 141 whose main axis is on the longitudinal axis of the plate element 10. This opening 141 is entirely surrounded by a recessed step 142.

Figure 4:
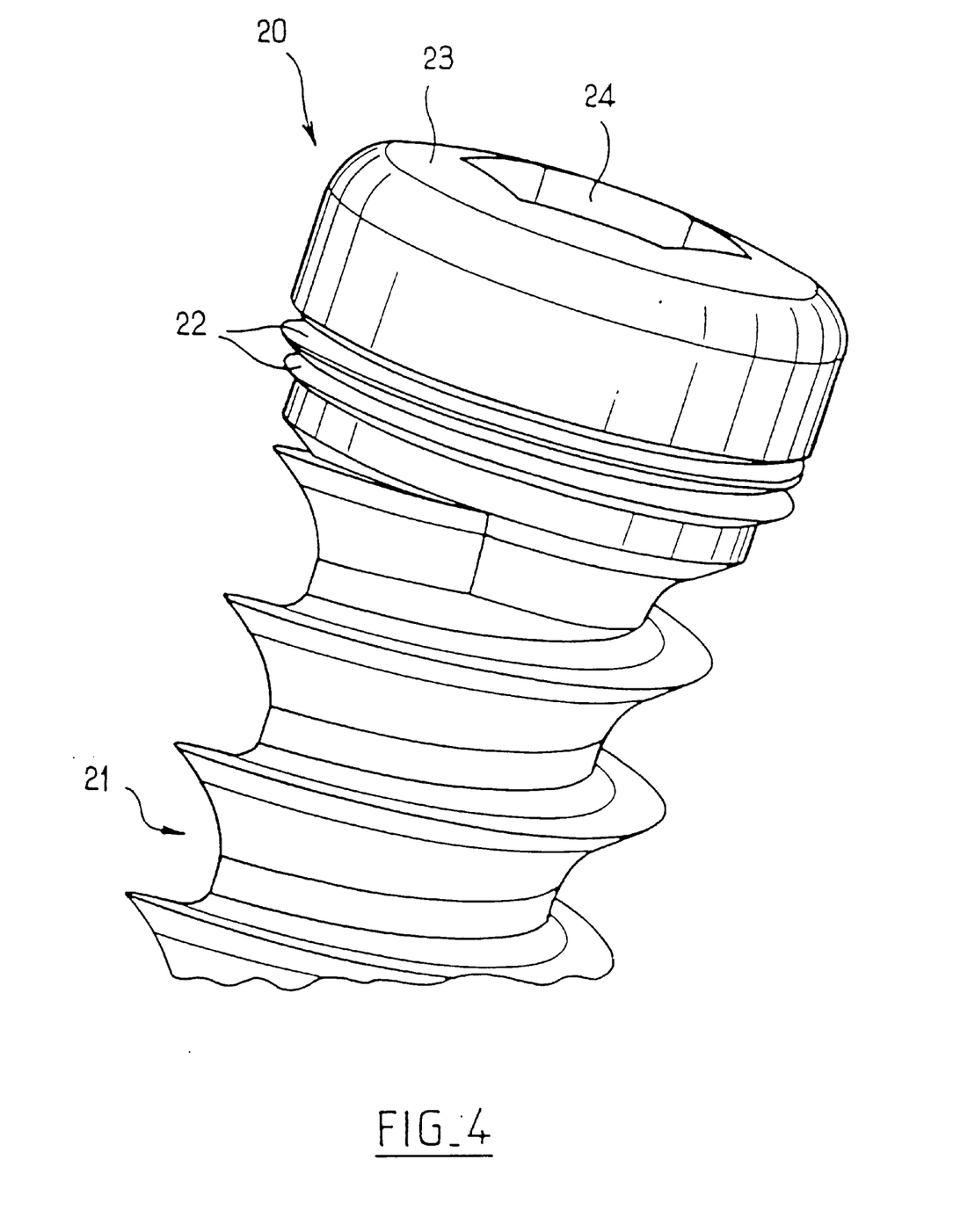
FIG. 4 is a perspective view, on an enlarged scale, of part of a bone fixation screw which can be used with the implant in FIGS. 1 to 3.

As is shown in particular in FIG. 4, each bone anchoring screw 20 principally comprises a threaded shank 21 intended to penetrate a cervical vertebra, and a wider head 23 in which there is a hollow hexagonal impression 24 for a screwing instrument. At the transition between the threaded part 21 and the head 23 there is also a thread 22 with a pitch substantially within that of the thread 21, extending over a very limited height and intended to cooperate with the thread 1111 provided in the associated opening 111 of the plate element, for reasons which will be explained below.

Finally, the screw 20 has, in the region of its tip, a concave recess 25 with sharp edges intended to facilitate the attack on the bone substance by the threads.

Finally, the implant according to the invention has two other screws 30, each having a short threaded part 31 allowing it to be screwed into an associated bore 121 of the plate element 10, by passing freely through the oblong opening 141 of the other plate element 10, and a head 32 having a groove for the screwing, and the width of which is very slightly smaller than the width between the opposite steps provided around the said opening 141.

The two plate elements 10, 10 are assembled by arranging these two elements head to tail, and by placing the end part 14 of each one over the intermediate part 12 of the other.

The two screws 30 are then put in place through the respective openings 141 and are screwed into the respective bores 121, but without blocking them.

It will be appreciated that from this moment onwards the two plate elements 10, 10 are joined to each other while at the same time retaining a single degree of freedom by sliding between two limit stops in the axial direction. The course of this sliding, indicated by d in FIG. 2, is defined in particular by the length of the oblong openings 141, and it is chosen to be equal to a few millimetres, for example two millimetres. It will be noted here that the limits on this mutual sliding movement are defined not only by the ends of the oblong openings 141 against which the screws 30 bear, but possibly also, in the opposite direction, by the shoulders 1311, 1321 of each element 10, described above, bearing respectively against the opposite faces of the intermediate part 12 and of the end part 14 of the other element 10.

It will also be noted that when the two plate elements 10, 10 are assembled, a through-passage is defined in the central region of the plate thus obtained, this through-passage being oblong in the axial direction, designated by reference 150, and defined jointly by the intermediate joining parts 13, 13 of the two elements 10, 10. This passage has, in its base region, a continuous peripheral oblique shoulder defined jointly by the faces 1312 provided on the two plate elements, which shoulder reduces the cross-section of the said passage, for reasons explained below.

The surgeon first introduces bone grafts into the intervertebral space situated between the two cervical vertebrae in which the implant is to be anchored, these bone grafts being intended in the long term to provide bone fusion between the two vertebrae.

Then, the implant first being prepared by introducing the four bone anchoring screws 20 into their respective four openings 111, the surgeon screws them in pairs into two adjacent vertebrae.

During this operation, the two plate elements 10, 10 can either be blocked, one in relation to the other, with the aid of screws 30 in a position of maximum distraction (position in FIG. 2) or can be free to slide relative to one another.

Once the bone anchoring screws 20 have been tightened, their intermediate threads 22 are able to cooperate with the threads 1111 provided in their respective openings 111 to ensure that they are blocked at the root of the thread and thus to prevent their loosening.

Then, the screws 30 being loosened if necessary, the surgeon closes the vertebrae together with the aid of an appropriate instrument, the effect of this being to compress the bone grafts and to make it easier for these grafts to take. During this movement, the two plate elements 10, 10 slide relative to one another. When the required degree of compression is reached, the assembly is held in this position and the two screws 30 are tightened in order to block the cervical plate in this position so as to ensure lasting compression of the grafts.

It will be noted here that, as a result of the dual overlapping of the two plate elements 10, on the one hand between the intermediate part 12 of the first and the end part 14 of the other and, in the opposite direction and at a distance, between the intermediate part 12 of the other and the end part 14 of the first, a plate is ultimately obtained which has excellent rigidity, especially with regard to bending.

It will also be noted here, as is shown in particular in FIGS. 1 and 3, that the bone anchoring screws 20 can be oriented in an inclined manner in relation to the perpendicular to the general plane of the cervical plate 10, 10.

More precisely, the through-openings 111 of the elements 10 can have their axes inclined either towards the outside of the plate or towards the inside, and both in its longitudinal direction as well as in its transverse direction, in order to adapt the orientation of the threaded shanks 21 of the screws 20 to the osseous configuration of the patient.

This inclination can be typically between 0° and 15° in one direction or the other.

In practice, different sets of plates with different numbers and/or different inclinations of the openings 111 are made available to the surgeon.

It should be noted here that the screws 20 with intermediate thread 22, cooperating with holes for screws 111 provided with an associated thread 1111, can be used not only with plates made up of two parts according to the present invention, but more generally in any sort of implant through which a bone anchoring screw is intended to pass.

Figure 5:
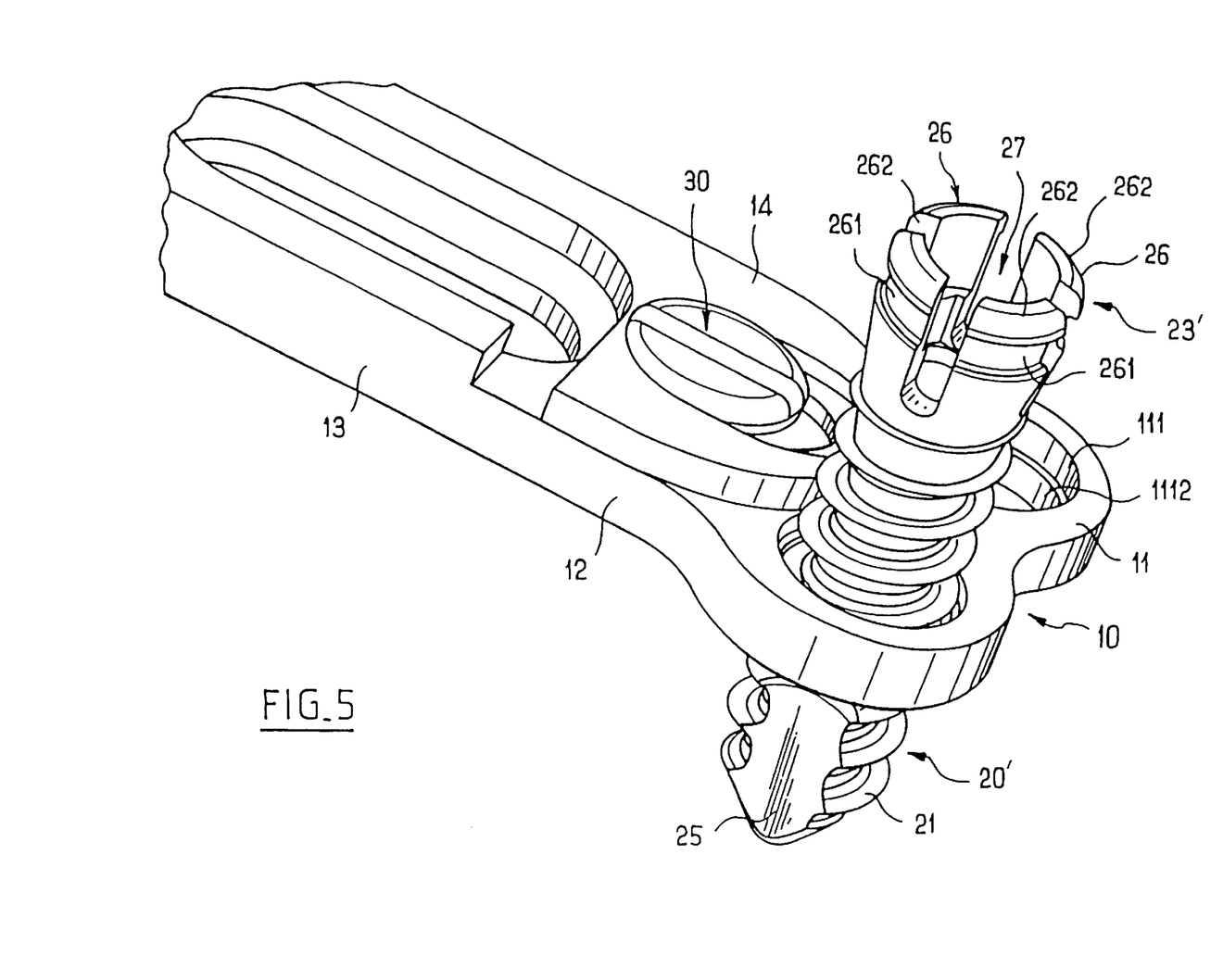
FIG. 5 is a perspective view of part of the implant and of a bone fixation screw according to another embodiment, before the screw has been screwed into a vertebra.
Figure 6:
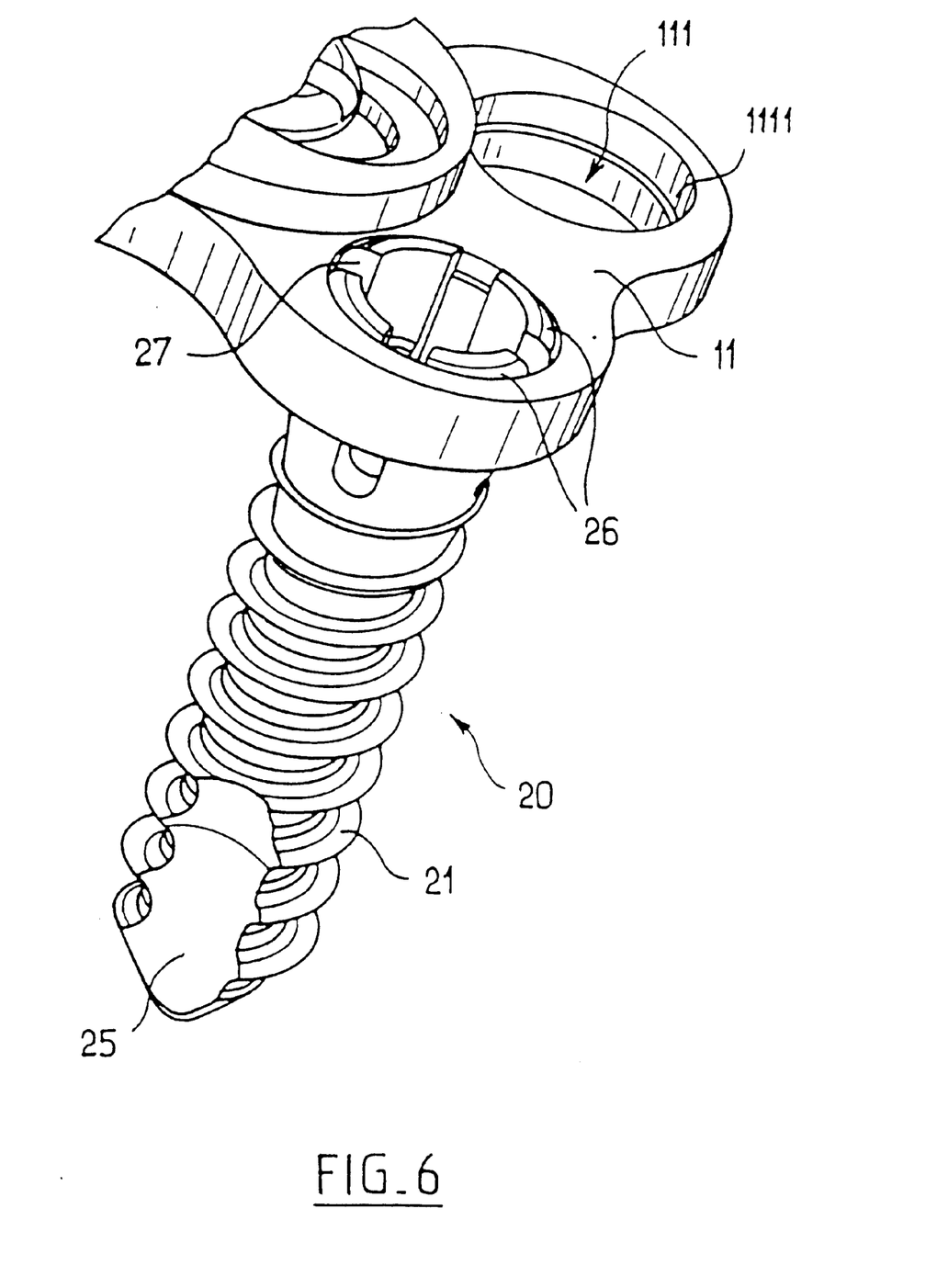
FIG. 6 is a view identical to that of FIG. 5, after screwing into a vertebra.

FIGS. 5 and 6 illustrate another embodiment of the anchoring screws, designated by 20'.

These screws comprise, in addition to the bone thread 21 and the recess 25, a hollow head 23' of circular cross-section and slightly frustoconical, the external diameter of which head is close to that of the threaded part. The conicity of the head 23' is such that its cross-section diminishes from its outer end towards the threaded shank 21.

This cylindrical head has four branches 26 which are uniformly spaced in the circumferential direction and which are separated by axially oriented interstices 27.

Each branch has a circumferential groove 261 on its outer face, and a locking tooth 262 is thus defined between the said groove and the free end of the head.

The head also has an indentation for screwing instruments which is provided in the root area of the four branches 26 and is not visible.

Moreover, the openings 111 provided in the plate elements 10 for receiving the screws 20 no longer have a thread, but instead a step, indicated by 1112 in FIG. 5, provided at the base of the respective opening 111, the axial dimension of which is substantially equal to that of the groove 261 of each of the branches, and which projects inwards.

The screw 20' is put into place by screwing it into the bone and, as it advances, the head 23' engages in the opening 111, the branches 26 then deforming elastically inwards under the effect of the stress exerted by the step 1112, until the latter comes to fit snugly in each of the four grooves 261.

Moreover, the dimension and the angle of conicity of the head 23' and the dimension of each associated opening 111 are such that at the end of tightening, the frictional force between the outer surface of the head and the wall of the associated opening 111 is sufficient to prevent loosening of the bone fixation screw 20'.

The embodiment illustrated in FIGS. 5 and 6 is advantageous in that, upon completion of the fitting procedure, the outer face of each screw 20' is substantially flush with the outer face of the part 11 of the plate 20, which reduces the overall space taken up by the assembly.

Figure 7:
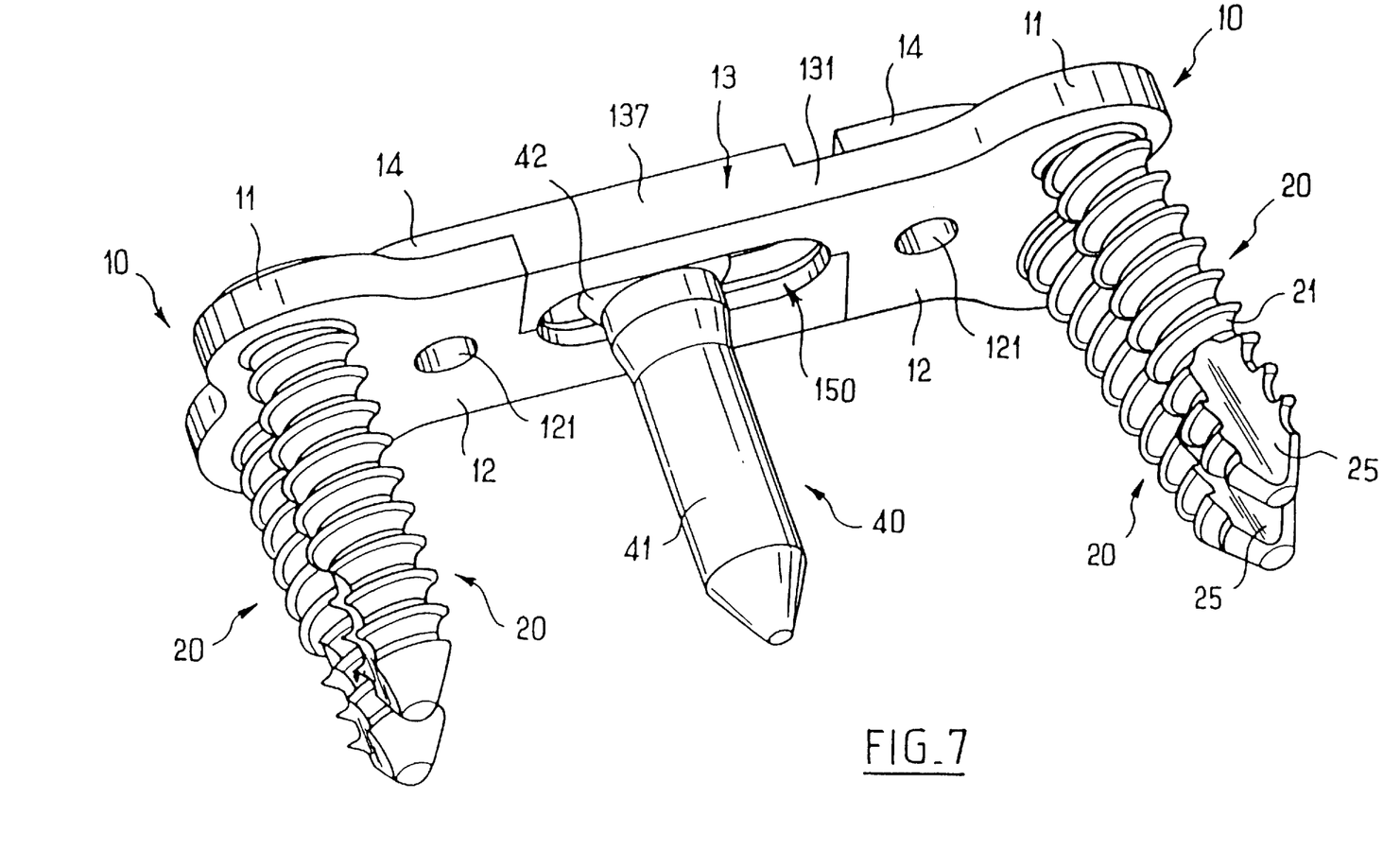
FIG. 7 is a perspective view of an implant according to FIGS. 1 to 3 together with an intermediate screw.
Figure 8:
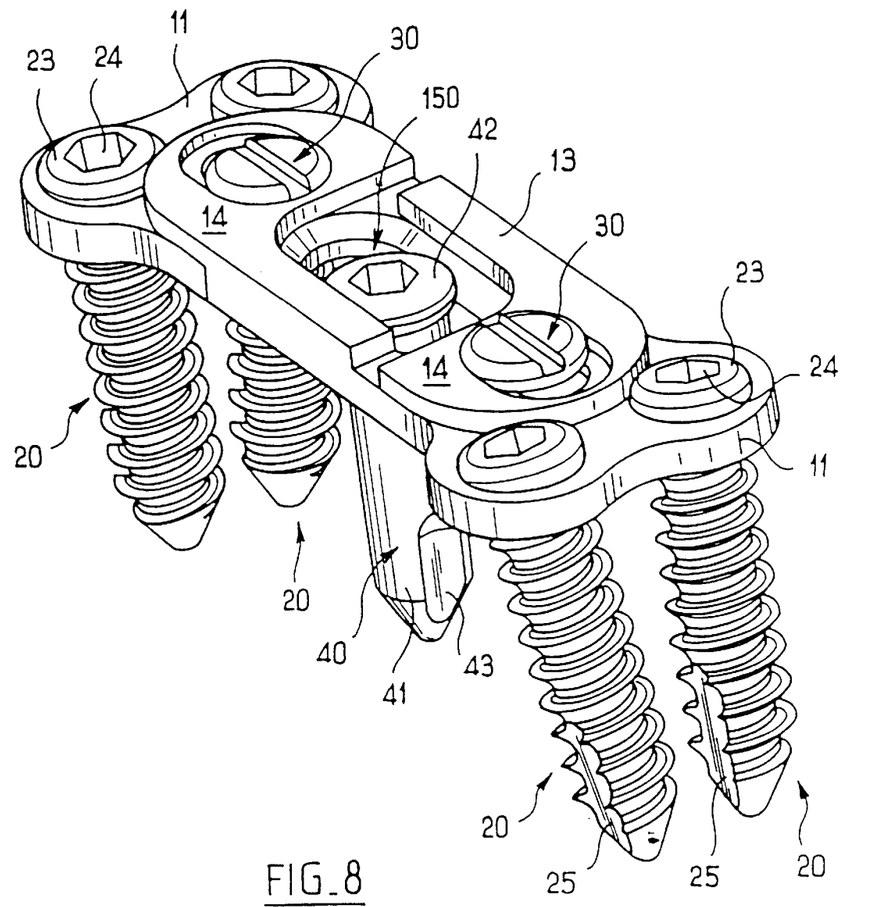
FIG. 8 is a perspective view, from another direction, of the implant in FIG. 7.

Referring now to FIGS. 7 and 8, the case is illustrated in which the implant forming the cervical plate described hereinabove is supplemented by a screw, shown diagrammatically by 40, which is intended to penetrate the bone graft placed between the two vertebrae, being put in place through the passage 150 defined by the two plate elements 10 during their assembly.

Such a screw comprises a shank 41, the thread of which has not been represented here for reasons of simplification, and a wider head 42, provided with a hollow hexagonal impression for a screwing instrument.

The overall diameter of the threaded shank 41 is smaller than the minimum width of the passage (at the area of the base regions 131 of the joining parts 13 of the elements 10), whereas the diameter of its head is greater than its maximum width (at the area of the regions 132 of the said parts 13).

In this way, the head 42 of the screw 40 cannot protrude outwards relative to the external contour of the assembled plate 10, 10, as is shown in FIG. 5.

This figure also shows that the threaded part 41 has, in the vicinity of its tip, a recess 43 facilitating the attack by the threads.

The addition of such a screw 40 improves the mechanical cohesion of the assembly, with the growth of bone taking place in engagement with the threads of this screw.

In addition, depending on the length of the oblong passage 150, it is possible to provide two or more screws 40 therein.

It will also be noted that the head 41 of the screw 40 has a base part 411 in the shape of a portion of a sphere, allowing the screw 40 to be easily inclined relative to the perpendicular to the general plane of the plate, in such a way as to adapt to the configuration of the intervertebral space receiving the bone grafts. The possible angulation can, for example, be as much as 20°.

Of course, the various components of the implants described hereinabove are made of a biocompatible material such as a titanium alloy or a stainless steel.

The present invention is of course not in any way limited to the embodiments which have been described and represented, and instead the skilled person will be able to make any variation or modification thereto in accordance with the spirit of the invention.

In particular, the number of bone anchoring screws 20 provided per element 10 can be other than two.

Moreover, the surgeon is preferably offered a box including a set of several implants and anchoring screws, with plate elements 10 having, for example, 1, 2, 3 or 4 holes 111 for fixation screws, and plate elements having different orientations of these holes 111 relative to the general plane of the part 11 of the elements.

In the box, these different elements 10 are differentiated, for example, by colour codes or the like.

What is claimed is:

1. An implant for osteosynthesis of the spine, comprising a plate having one end configured for attachment to a first vertebra and a second end configured for attachment to a second vertebra with the aid of bone fixation screws, said plate having first and second receiving elements, each element including a body portion with at least one hole for the bone fixation screws, each of the first and second element body portions being able to slide relative to the other in a direction corresponding to a closing together or distancing of the two vertebrae relative to one another and said first and second elements each being provided with means associated with each element for selectively allowing the free sliding of said elements or locking the said elements in a position chosen from among a plurality of positions in said direction defined by the mutual sliding engagement between the said elements.

2. The implant according to claim 1, wherein the at least one hole in each body portion of the first and second elements are arranged adjacent said first and second vertebrae respectively.

3. The implant according to one of claims 1 or 2, wherein the first and second elements are identically shaped.

4. The implant according to claim 2, wherein the first and second elements each include a first end part including the at least one hole for bone fixation screws and a second end part including said means for selectively allowing sliding, said means having an oblong opening whose main axis defines the direction of sliding, said oblong opening being traversed by a projecting element engageable with an intermediate part of the other element.

5. The implant according to claim 4, wherein each projecting element consists of a screw.

6. The implant according to claim 4, wherein said intermediate part of each element is situated in an extension and continuation of said first end part.

7. The implant according to claim 6, wherein said second end part of said first and second elements is offset relative to said first end part and to the said intermediate part in such a way as to cover the intermediate part of the other element.

8. The implant according to claim 7, wherein each element additionally comprises a narrower joining part extending between its intermediate part and its second end part.

9. The implant according to claim 8, wherein said joining parts of the two elements each delimit part of a through-passage in the plate.

10. The implant according to claim 9, wherein said through-passage is oblong and has at a base thereof a peripheral shoulder.

11. The implant according to claim 10, wherein said shoulder is beveled.

12. The implant according to claim 8, wherein said joining part of each element defines at least one shoulder able to cooperate with the second end part or with the intermediate part of the other element, in such a way as to define a limit stop for the sliding of the two elements.

13. The implant according to claim 4, further comprising at least one auxiliary anchoring element extending through said intermediate part.

14. The implant according to claim 1, wherein each bone fixation screw includes an intermediate thread intended to cooperate with a corresponding thread provided in the hole for the associated screw.

15. The implant according to claim 1, wherein each bone fixation screw includes a head of generally frustoconical contour and provided with a plurality of branches which are separated by interstices of generally axial orientation, the frustoconical contour of the head being able to lock the screw against rotation by means of the friction of the said head in the associated hole.

16. The implant according to claim 15, wherein said head has a groove able to cooperate with an inwardly projecting part formed in the associated hole for producing axial locking.

17. The implant according to claim 1, wherein at least one of the holes for bone fixation screws has an axis not perpendicular to a general plane of the plate.

18. A method of attaching a plate to two vertebrae, said plate intended to be fixed to the two vertebrae with the aid of bone fixation screws, the plate comprising first and second elements, each including at least one hole for a bone fixation screw, each of the elements being able to slide relative to the other in a direction corresponding to a closing together or distancing of the vertebrae relative to one another, and each of said elements being provided with a separate means for selectively allowing free sliding of said first element with respect to said second element and for selectively locking said elements in a mutual position from among a plurality of positions defined in a given course of the mutual sliding engagement between said first and second elements, the method comprising:

placing bone graft between the two vertebrae to be treated;

fixing the plate to the two vertebrae, by attaching said first and second element to respective vertebrae with the aid of said screws, in a position in which the two elements occupy a first mutual position adapted to the existing spacing between the two vertebrae;

exerting on the two vertebrae a movement which moves them toward one another, tending to compress the bone graft, this movement displacing, by sliding motion, the two elements from their first mutual position; and locking the two elements relative to one another by actuation of said separate selective locking means when the desired distance between the vertebrae, corresponding to a second mutual position of the elements, has been reached.

19. A kit of plates for connecting a pair of vertebrae comprising:

a plurality of first elements each having at least one bone screw receiving hole at a first end and an oblong slot at a second end;

a plurality of second elements for sliding engagement with said first element at least in the area of said slots and having at least one bone screw receiving hole at a first end thereof and an oblong slot at a second end; and locking elements for extending through each of said slots in said first and second elements and into engagement with a corresponding one of said first and second elements for preventing said sliding engagement between said first and second elements.

20. The plates as set forth in claim 19, wherein said locking elements are screws.

21. The plates as set forth in claim 20, wherein said screws have a head with an element for lockingly engaging said oblong opening.

* * * * *

UNITED STATES PATENT AND TRADEMARK OFFICE
CERTIFICATE OF CORRECTION

PATENT NO. : 6,306,136 B1
DATED : October 23, 2001
INVENTOR(S) : Christian Baccelli It is certified that error appears in the above-identified patent and that said Letters Patent is hereby corrected as shown below:

<u>Title page,</u>
Title, line 1, "FRONT" should read -- AN ANTERIOR --.

<u>Column 1,</u>
Line 1, "FRONT" should read -- AN ANTERIOR --.

Signed and Sealed this

Ninth Day of April, 2002

Attest:

Attesting Officer

JAMES E. ROGAN
*Director of the United States Patent and Trademark Office*